(12) United States Patent
Qing et al.

(10) Patent No.: US 7,395,189 B2
(45) Date of Patent: Jul. 1, 2008

(54) METHOD AND APPARATUS FOR SWITCHING AMONG ELEMENTS OF A STRUCTURAL HEALTH MONITORING SYSTEM

(75) Inventors: Xinlin Qing, Cupertino, CA (US); Shawn J. Beard, Livermore, CA (US); Zengpin Yu, Palo Alto, CA (US); Irene Li, Stanford, CA (US)

(73) Assignee: Acellent Technologies, Inc., Sunnyvale, CA (US)

( * ) Notice: Subject to any disclaimer, the term of this patent is extended or adjusted under 35 U.S.C. 154(b) by 23 days.

(21) Appl. No.: 11/600,248

(22) Filed: Nov. 14, 2006

(65) Prior Publication Data

US 2007/0165218 A1 Jul. 19, 2007

Related U.S. Application Data

(60) Provisional application No. 60/737,018, filed on Nov. 14, 2005.

(51) Int. Cl.
*G06F 11/30* (2006.01)
*G21C 17/00* (2006.01)

(52) U.S. Cl. ..................... 702/185; 702/188
(58) Field of Classification Search .............. 702/182, 702/185, 188, 33; 73/862.046, 760, 763
See application file for complete search history.

(56) References Cited

U.S. PATENT DOCUMENTS

| | | | |
|---|---|---|---|
| 3,713,127 A | 1/1973 | Keledy et al. | |
| 3,822,586 A | 7/1974 | Pollock | |
| 3,858,439 A | 1/1975 | Nakamura | |
| 3,924,456 A | 12/1975 | Vahaviolos | |
| 3,956,731 A | 5/1976 | Lewis, Jr. | |
| 4,006,625 A | 2/1977 | Davis | |
| 4,107,981 A | 8/1978 | Kanagawa et al. | |
| 5,176,032 A | 1/1993 | Holroyd et al. | |

(Continued)

FOREIGN PATENT DOCUMENTS

DE  4237404  5/1994

(Continued)

OTHER PUBLICATIONS

Roh, Youn-Seo, et al., "*Effect of Impact Damage on Lamb Wave Propagation in Laminated Composites*" Department of Aeronautics and Astronautics, Stanford University, Stanford, CA 94305 (1995) pp. 1-12.

(Continued)

*Primary Examiner*—Bryan Bui
(74) *Attorney, Agent, or Firm*—MacPherson Kwok Chen & Heid LLP (57) ABSTRACT

Use of a single line for switching multiple monitoring elements on/off, and a single line for sending signals to, or receiving signals from, those elements that are switched on. Monitoring elements each have an associated switching element, and each switching element is connected to a common switching line, or control line. A signal from the control line turns each switch on or off. Each monitoring element is also connected to a single signal line, and only those monitoring elements that are turned on can transmit/receive data signals along this signal line.

16 Claims, 6 Drawing Sheets

U.S. PATENT DOCUMENTS

| | | | |
|---|---|---|---|
| 5,195,046 | A | 3/1993 | Gerardi et al. |
| 5,298,964 | A | 3/1994 | Nelson et al. |
| 5,714,687 | A | 2/1998 | Dunegan |
| 5,774,376 | A | 6/1998 | Manning |
| 5,814,729 | A | 9/1998 | Wu et al. |
| 6,006,163 | A | 12/1999 | Lichtenwalner et al. |
| 6,065,342 | A | 5/2000 | Kerr et al. |
| 6,170,334 | B1 | 1/2001 | Paulson |
| 6,252,334 | B1 | 6/2001 | Nye et al. |
| 6,370,964 | B1 * | 4/2002 | Chang et al. ........... 73/862.046 |
| 6,399,939 | B1 | 6/2002 | Sundaresan et al. |
| 6,418,384 | B1 | 7/2002 | Rothea et al. |
| 6,529,127 | B2 | 3/2003 | Townsend et al. |
| 6,691,007 | B2 | 2/2004 | Haugse et al. |
| 6,693,548 | B2 | 2/2004 | Boyce et al. |
| 6,768,312 | B2 | 7/2004 | Sun et al. |
| 6,826,982 | B2 | 12/2004 | O'Brien et al. |
| 6,964,201 | B2 | 11/2005 | Xu et al. |
| 7,038,470 | B1 | 5/2006 | Johnson |
| 7,075,424 | B1 | 7/2006 | Sundaresan |
| 7,103,507 | B2 | 9/2006 | Gorinevsky |
| 7,117,742 | B2 | 10/2006 | Kim |
| 7,118,990 | B1 | 10/2006 | Xu et al. |
| 7,201,035 | B2 | 4/2007 | Sunshine |
| 7,246,521 | B2 | 7/2007 | Kim |
| 2001/0047691 | A1 | 12/2001 | Dzenis |
| 2002/0154029 | A1 | 10/2002 | Watters et al. |
| 2003/0164700 | A1 | 9/2003 | Goldfine et al. |
| 2004/0002815 | A1 | 1/2004 | Ishizak et al. |
| 2004/0032013 | A1 | 2/2004 | Cobbley et al. |
| 2005/0072249 | A1 | 4/2005 | Maeda et al. |
| 2006/0079747 | A1 | 4/2006 | Beard et al. |
| 2006/0149449 | A1 | 7/2006 | Baur et al. |
| 2006/0154398 | A1 | 7/2006 | Qing et al. |
| 2006/0179949 | A1 | 8/2006 | Kim |
| 2006/0283266 | A1 | 12/2006 | Qing et al. |
| 2007/0018083 | A1 | 1/2007 | Kumar et al. |

FOREIGN PATENT DOCUMENTS

| | | |
|---|---|---|
| DE | 19835561 | 2/2000 |
| DE | 10217031 | 10/2003 |

OTHER PUBLICATIONS

Keilers, Charles Henry Jr., "*Damage identification in Composites Using Built-in Piezoelectrics: A Dissertation Submitted to the Department of Aeronautics and Astronautics and the Committee on Graduate Studies of Stanford University in Partial Fulfillment of the Requirements for the Degree of Doctor of Philosophy*", pp. 1-111 (Jun. 1993).

Roh, Youn-Seo, "*Built-in Diagnostics for Identifying an Anomaly in Plates Using Wave Scattering*", UMI Microform 9924496, UMI Company, ANn Arbor, MI (1999) pp. iv-88.

Chang, Fu-Kuo, "Built-in Damage Diagnostics for Composite Structures" Department of Aeronautics and Astronautics, Stanford University, Stanford, CA 94305 (1995).

* cited by examiner

METHOD AND APPARATUS FOR SWITCHING AMONG ELEMENTS OF A STRUCTURAL HEALTH MONITORING SYSTEM

This application claims the benefit of U.S. Provisional Patent Application No. 60/737,018, filed on Nov. 14, 2005, the disclosure of which is hereby incorporated by reference in its entirety and for all purposes.

BRIEF DESCRIPTION OF THE INVENTION

The present invention relates generally to structural health monitoring. More specifically, the present invention relates to a method and apparatus for switching among sensing elements in a structural health monitoring system.

BACKGROUND OF THE INVENTION

The diagnostics and monitoring of structures, such as that carried out in the structural health monitoring field, are often accomplished by employing arrays of monitoring elements such as sensors, actuators, and/or transducers. While many advances have been made, the field continues to face challenges. For example, such arrays often require large numbers of monitoring elements in order to be effective, as structures often must have a variety of sensing elements placed at various locations for accurate monitoring. Because individual sensing elements must often be placed separately, affixing a large array of such sensing elements can be tedious and time consuming. In addition, as each individual sensing element can require one or, commonly, multiple wires, large arrays of sensing elements can require a large number of individual wires, which may be difficult to handle and keep track of. The securing of such large numbers of wires can often be painstaking and time consuming, as well. It is therefore desirable to reduce the number of wires used in arrays of structural health monitoring elements.

SUMMARY OF THE INVENTION

The invention can be implemented in numerous ways, including as a method, apparatus, or computer readable medium. Several embodiments of the invention are discussed below.

In one embodiment of the invention, a structural health monitoring system comprises a plurality of monitoring elements configured for coupling to a structure, and a plurality of switches each in electrical communication with an associated monitoring element of the plurality of monitoring elements, and each configured to switch the associated monitoring element to an on state and an off state. Also included are a control line configured for coupling to the structure, and in electrical communication with each switch of the plurality of switches, a signal line configured for coupling to the structure, and in electrical communication with each monitoring element of the plurality of monitoring elements, and a controller. The controller is configured to transmit a control signal along the control line so as to switch selected ones of the monitoring elements to the on state or the off state, and configured to perform at least one of transmitting a monitoring signal along the signal line to those monitoring elements switched to the on state so as to initiate a monitoring of the structure, or receiving a sensing signal along the signal line from those monitoring elements switched to the on state so as to facilitate the sensing of the structure.

In another embodiment of the invention, and in a structural health monitoring system including a plurality of monitoring elements configured for coupling to a structure, the monitoring elements each having an on state and an off state, a method of monitoring the health of a structure comprises selecting ones of the monitoring elements, and switching the selected ones of the monitoring elements to the on state. Also included is at least one of transmitting a monitoring signal to those monitoring elements switched to the on state so as to initiate a monitoring of the structure, or receiving a sensing signal from those monitoring elements switched to the on state so as to facilitate the sensing of the structure.

In another embodiment of the invention, and in a computer readable medium having computer executable instructions thereon for a method of monitoring the health of a structure in a structural health monitoring system including a plurality of monitoring elements configured for coupling to the structure, the monitoring elements each having an on state and an off state, the method comprises selecting ones of the monitoring elements and switching the selected ones of the monitoring elements to the on state. Also included is at least one of transmitting a monitoring signal to those monitoring elements switched to the on state so as to initiate a monitoring of the structure, or receiving a sensing signal from those monitoring elements switched to the on state so as to facilitate the sensing of the structure.

Other aspects and advantages of the invention will become apparent from the following detailed description taken in conjunction with the accompanying drawings which illustrate, by way of example, the principles of the invention.

BRIEF DESCRIPTION OF THE DRAWINGS

The invention, together with further objects and advantages thereof, may best be understood by reference to the following description taken in conjunction with the accompanying drawings in which.

Like reference numerals refer to corresponding parts throughout the drawings. Also, it is understood that the depictions in the figures are diagrammatic and not necessarily to scale.

DETAILED DESCRIPTION OF EMBODIMENTS OF THE INVENTION

In one sense, the invention relates to the use of a single line for switching multiple monitoring elements on/off, and a single line for sending signals to, or receiving signals from, those elements that are switched on. Monitoring elements each have an associated switching element, and each switching element is connected to a common switching line, or control line. A signal from the control line turns each switch on or off. Each monitoring element is also connected to a single signal line, and only those monitoring elements that are turned on can transmit/receive data signals along this signal line. In this manner, even large arrays of monitoring elements need use only two lines: a single control line, and a single signal line. This yields a structural health monitoring system that uses very few wires, and is thus simple and easy to install.

Initially, it should be noted that it is often preferable to employ the methods and apparatuses of the invention in conjunction with a flexible sensing layer. More particularly, while the invention is typically carried out as an array of monitoring elements, it is often preferable to affix these monitoring elements, and at least some of their wiring and/or control elements, to a flexible sensing layer that can be attached to a structure. The layer holds the monitoring elements, letting them carry out their monitoring functions upon the structure they are attached to. In this manner, only a single sensing layer need be attached to the structure, rather than a number of individual monitoring elements and their associated circuitry. It should also be noted, however, that the methods and apparatuses of the invention need not necessarily utilize such a flexible layer, but that the invention instead encompasses embodiments in which no layer is used.

Figure 1A:
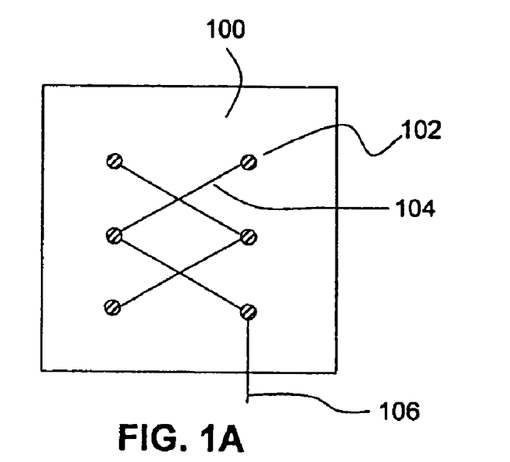
FIG. 1A illustrates a top view of a sensing layer manufactured in accordance with embodiments of the present invention.

FIG. 1A illustrates a flexible sensing layer for use in accordance with embodiments of the present invention. A diagnostic layer 100 is shown, which contains an array of sensors 102. The sensors 102 can be sensors capable of receiving signals used in structural health monitoring such as stress waves, and are connected to conductive traces 104. The traces 104 connect (or interconnect, if necessary) sensors 102 to one or more output leads 106 configured for connection to a processor or other device capable of analyzing the data derived from the sensors 102.

Figure 1B:
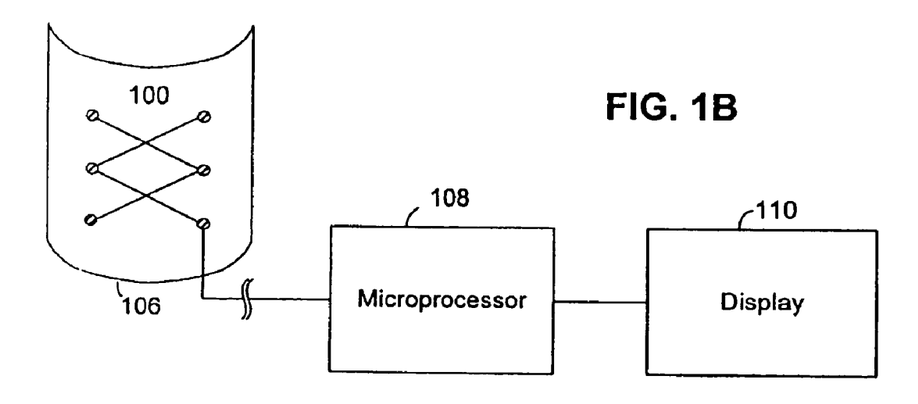
FIGS. 1B-1C illustrate block and circuit diagrams, respectively, describing elements of a sensing layer and their operation.

The diagnostic layer 100 and its operation are further described in U.S. Pat. No. 6,370,964 to Chang et al., which is hereby incorporated by reference in its entirety and for all purposes. Construction of the diagnostic layer 100 is also explained in U.S. patent application Ser. No. 10/873,548, filed on Jun. 21, 2004, which is also incorporated by reference in its entirety and for all purposes. It should be noted that the present invention is not limited to the embodiments disclosed in the aforementioned U.S. patent application Ser. No. 10/873,548, but instead encompasses the use of flexible sensor layers having any configuration. For illustration, FIG. 1B further describes aspects of the operation of the diagnostic layer 100. In operation, the output leads 106 are electrically connected to an analysis unit such as a microprocessor 108, suitable for analyzing signals from the sensors 102. In certain embodiments, the flexible layer 100 is first attached to a structure in a manner that allows the sensing elements 102 to detect quantities related to the health of the structure. For instance, the sensors 102 can be sensors configured to detect stress waves propagated within the structure, and emit electrical signals accordingly. The microprocessor 108 then analyzes these electrical signals to assess various aspects of the health of the structure. For instance, detected stress waves can be analyzed to detect crack propagation within the structure, delamination within composite structures, or the likelihood of fatigue-related failure. Quantities such as these can then be displayed to the user via display 110.

Figure 1C:
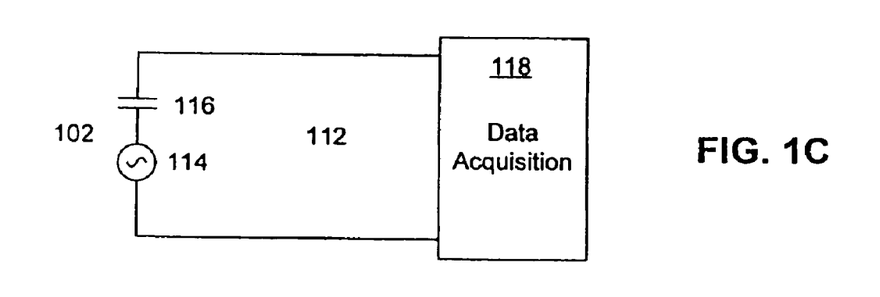

In one embodiment, the sensors 102 can be piezoelectric transducers capable of reacting to a propagating stress wave by generating a voltage signal. Analysis of these signals highlights properties of the stress wave, such as its magnitude, propagation speed, frequency components, and the like. Such properties are known to be useful in structural health monitoring. FIG. 1C illustrates a circuit diagram representation of such an embodiment. This embodiment can often be represented as a circuit 112, where each sensor 102 is represented as a voltage source 114 in series with a capacitor 116 (impedance circuitry) used to adjust signal strength. This pair is in electrical contact with a data acquisition unit 118, such as a known data acquisition card employed by microprocessors 108 (the data acquisition unit 118 can be thought of as a component interface to the microprocessor 108). Propagating stress waves induce the sensor 102 to emit a voltage signal that is recorded by the data acquisition unit 118, where it can be analyzed to determine the health of the structure in question. As discussed below, these piezoelectric transducers can also act as actuators, converting an applied voltage to a stress wave signal. In another embodiment, the sensors 102 can be known fiber optic sensors that convert stress waves to optical signals.

Figure 2A:
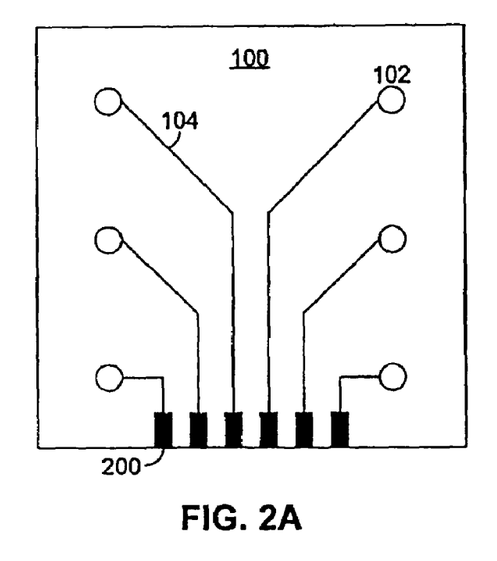
FIG. 2A illustrates a top view highlighting further details of a sensing layer having a two-dimensional array of monitoring elements.
Figure 2B:
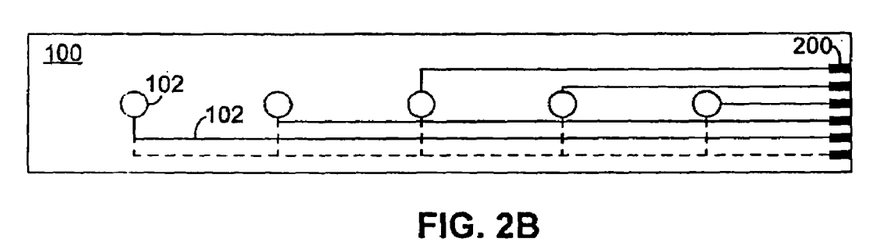
FIG. 2B illustrates a top view highlighting further details of a sensing layer having a one-dimensional array of monitoring elements.

FIG. 2A illustrates further details of a sensing layer 100. It should be noted that the invention includes sensing layers 100 configured in any number of ways. For instance, the sensors 102 can be distributed in any manner throughout the layer 100. Here, six such sensors 102 are shown regularly distributed in a two-dimensional array, each with a single trace 104 extending to the contacts 200. However, one of skill will observe that the sensors 102, traces 104, and contacts 200 can be distributed in any manner, and in any number, without departing from the scope of the invention. For example, the sensors 102 can also be configured in a one-dimensional array such as that shown in FIG. 2B. Here, instead of two rows of sensors 102, a single row is employed. Such a one-dimensional array finds uses in, for example, the monitoring of areas too narrow to fit a two-dimensional array.

Figure 3:
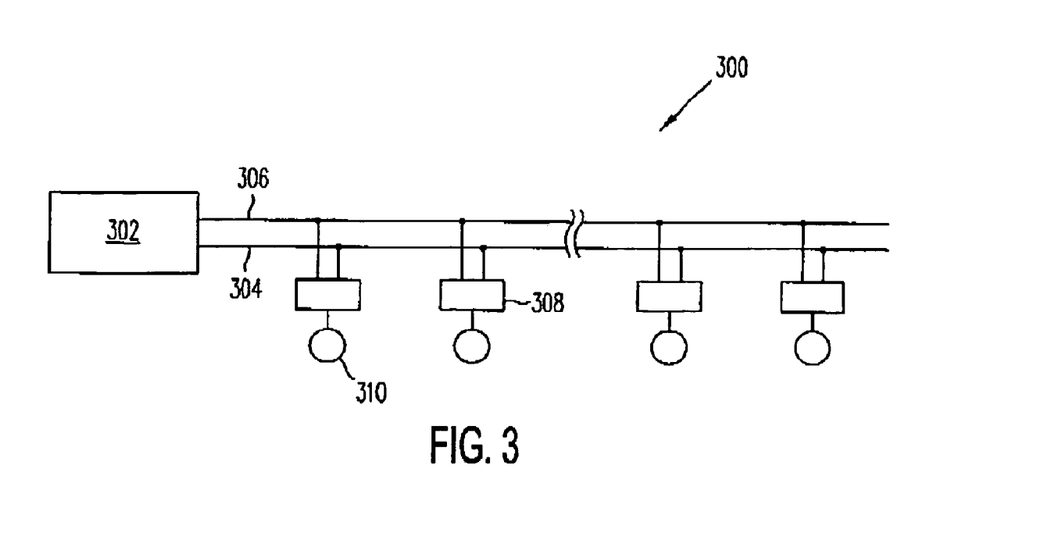
FIG. 3 illustrates a system employing an array of actuators, a single control line, and a single signal line, in accordance with embodiments of the present invention.

In the following description, one of ordinary skill in the art will observe that the systems and methods described can be implemented in conjunction with a flexible layer described above, and can also be implemented without one. As one example, FIG. 3 illustrates a system employing an array of actuators, a single control line, and a single signal line. Here, the sensor system 300 includes a controller 302 connected to a control line 304 and a signal line 306. A number of switches 308 are connected to the control line 304 and the signal line 306. Also, each switch 308 has an actuator 310 connected to it.

In operation, the actuators 310 are affixed to a structure, and controller 302 transmits a control signal along the control line 304, identifying the actuators 310 it desires to turn on. The control signal switches the corresponding switches 308 to the on state, whereupon the controller 302 can transmit a signal along the signal line 306. As the actuators 310 are each connected to the signal line 306 through their respective switches 308, this signal only reaches those actuators 310 whose switches 308 are turned on. In this manner, a single control line 304 can be used to select actuators 310 for activation, after which a single signal line 306 can be used to transmit monitoring signals to only those actuators 310 that have been selected. It can be seen that different actuators 310 can be turned on and off in this same manner as necessary, so as to perform structural health monitoring operations on different parts of the structure at different times while utilizing only a single pair of wires.

The actuators 310 and signals can be any elements, and their corresponding signals, employed in monitoring the health of a structure. In one embodiment, the actuators 310 are piezoelectric transducers that convert electrical signals to stress waves that propagate within the structure they are attached to, and likewise also convert received stress waves to electrical signals. In this embodiment, the signals transmitted along the signal line 306 correspond to a stress wave having a desired profile. The transducers whose switches 308 are turned on would thus receive this signal, and convert it to stress waves within the structure. These stress waves could then be picked up, perhaps by other transducers whose switches 308 are also in the on state. The detected stress waves are then converted by these transducers back into an electrical signal that is sent along the signal line 308 to the controller 302 for processing.

Figure 4:
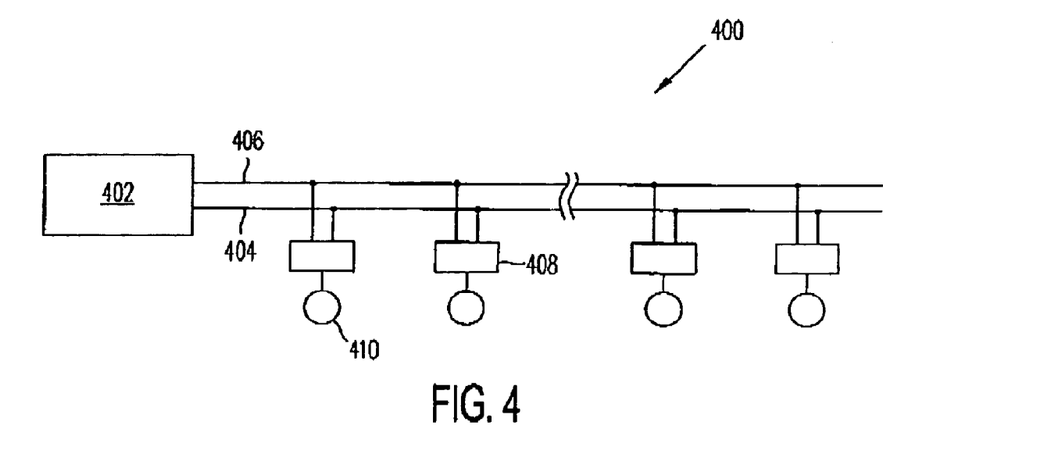
FIG. 4 illustrates a system employing an array of sensors, a single control line, and a single signal line.

One of ordinary skill in the art will observe that the invention can be employed in sensing, as well as actuation. FIG. 4 illustrates a system employing an array of sensors, a single control line, and a single signal line. Here, the system 400 includes a controller 402, connected to a control line 404 and a signal line 406. A number of switches 408 are connected to the control line 404 and the signal line 406. Also, each switch 408 has a sensor 410 connected to it. The system 400 is configured similar to the system 300 of FIG. 3, except that the system 400 employs sensors 410 instead of actuators 310. In operation, the controller 402 sends a control signal along its control line 404, switching the switches 408 of desired sensors 410 to their on state. The sensors 410 whose switches 408 are switched on can thus monitor the structure they are attached to, and send corresponding electrical signals along the signal line 406 to the controller 402. In this manner, a network of sensors 410 can be controlled using only a signal line 406 and control line 404, instead of one or more wires for each individual sensor 410.

Figure 5:
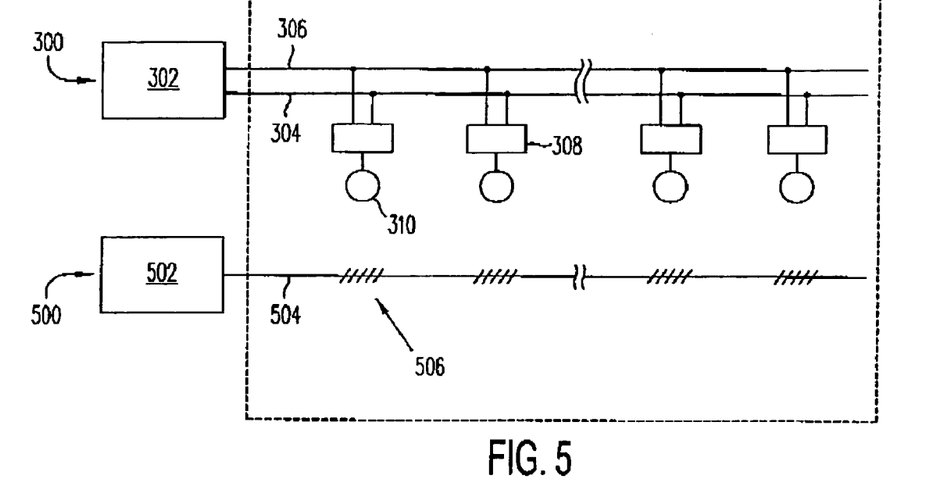
FIG. 5 illustrates a system employing an array of actuators, a single control line, and a single signal line, and also employing an array of sensors.
Figure 6:
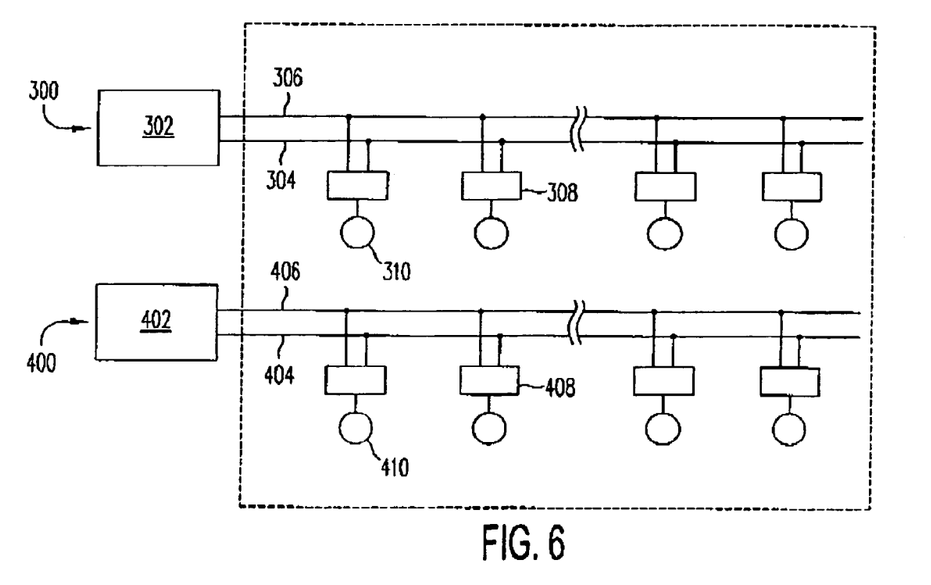
FIG. 6 illustrates a system employing an array of actuators with a single control line and a single signal line, as well as an array of sensors with a single control line and a single signal line.

The actuators and sensors can also be connected to separate networks, as shown in FIG. 5. Here, the actuator system 300 of FIG. 3 is employed along with a sensing system 500, which includes a controller 502 connected to a signal line 504 that has sensing elements 506. In the embodiment shown, the sensing elements 506 shown are known fiber optic sensors, and the signal line 504 is a fiber optic line, however the invention includes the use of any sensors. In operation, the system 300 and the system 500 are attached to the same structure. The system 300 can then be employed to generate stress waves in the structure as above, where the stress waves are detected by the sensing elements 506 of the sensing system 500. Similarly, as shown in FIG. 6, the invention can employ an actuator system 300 and a sensing system 400 such as that desexibed in FIG. 4. Here, the actuator system 300 can transmit stress waves through a structure as described above, and these stress waves can be detected by the sensors 410 of the sensing system 400.

Figure 7:
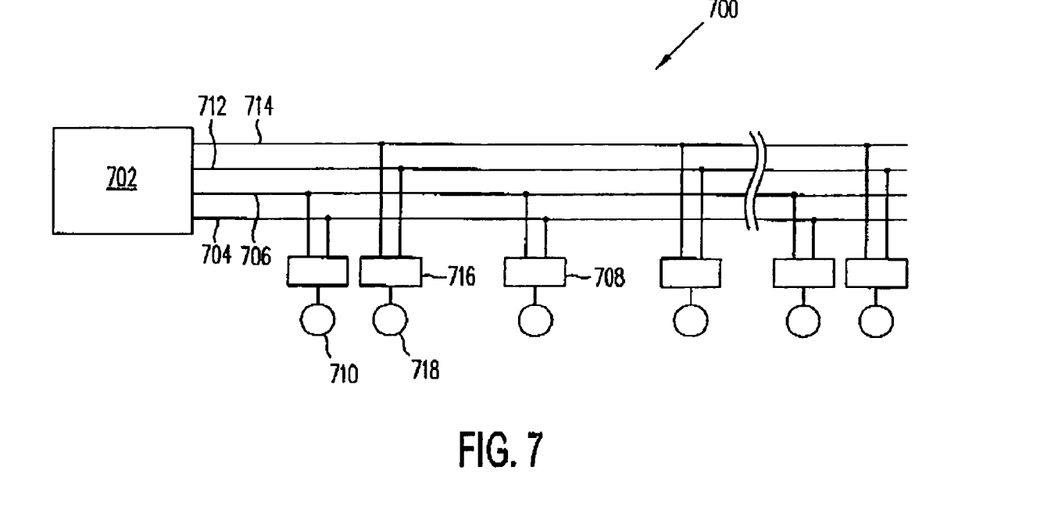
FIG. 7 illustrates a system employing an array of actuators and sensors, a single control line, and a single signal line.

While FIGS. 3 and 4 illustrate networks of actuators and sensors respectively, it should be recognized that the invention can also employ networks containing both actuators and sensors simultaneously. For example, in system 400 of FIG. 4, the sensors 410 can be either actuators (such as actuators 308) or sensors 410. Those actuators whose switches 408 are in the on state can thus receive signals from the signal line 406 and transmit corresponding stress waves through the structure, whereupon the transmitted stress waves can be detected by sensors 410 whose switches 408 are in the on state. The detected stress waves are then converted to electrical signals and sent back along the signal line 406. It is sometimes also desirable to employ separate signal and control lines for actuators and sensors, i.e., one signal line/control line pair for the actuators, and a separate signal line/control line pair for the sensors. FIG. 7 illustrates such a configuration. Here, a sensor/actuator system 700 has a controller 702 connected to a first control line 704 and a first signal line 706. These lines 704, 706 are connected to switches 708, which are in turn connected to actuators 710. Similarly, the controller 702 is also connected to a second control line 712 and second signal line 714. The lines 712, 714 are connected to switches 716, which are connected to sensors 718. Typically, the actuators 710 and sensors 718 are attached to a structure at differing locations. As above, the controller 702 can then switch on certain actuators 710 via the first control line 704 and switches 708, and can then transmit signals along the first signal line 706 to these actuators 710, thus generating a stress wave in the structure. Simultaneously, the controller 702 can also switch on certain sensors 718 via the second control line 712 and switches 716. These sensors 718 can detect the stress wave after it has propagated through the structure, converting the sensed wave to electrical signals and transmitting these signals along the second signal line 714 for processing.

Figure 8:
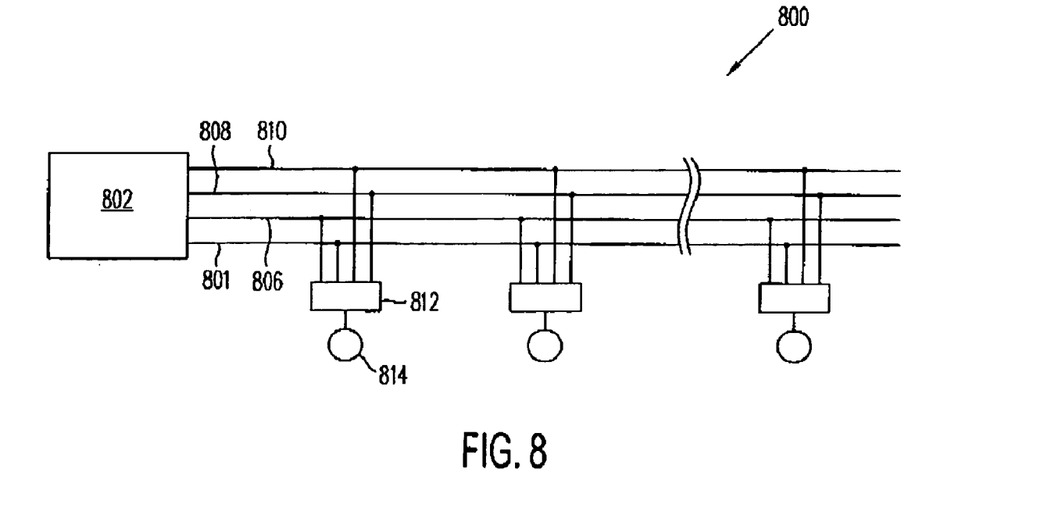
FIG. 8 illustrates a system employing an array of transducers, a single control line, and a single signal line.

In embodiments employing transducers or other combined sensor/actuators, the same monitoring elements can act as both actuators and sensors, while still being controlled by a single switch. FIG. 8 illustrates a system 800 employing an array of transducers, a single control line, and a single signal line. Here, a controller 802 has a first control line 804 and a first signal line 806, as well as a second control line 808 and second signal line 810. Each of these lines 804-810 are connected to switches 812, which are each connected to a transducer 814. In operation, the controller 802 can transmit control signals along the first control line 804 to switch selected transducers 814 on/off for actuation, and can then transmit signals along the first signal line 806 to cause those transducers to generate stress waves in the structure being monitored. The controller 802 can also transmit control signals along the second control line 808 to switch other transducers 814 on/off for sensing. These transducers 814 then sense stress waves, convert them to electrical signals, and transmit them along the second signal line 810 back to the controller 802. Configurations like this one allow a network of transducers to be controlled by only four lines 804-810, rather than one or more lines for each transducer 814.

Figure 9:
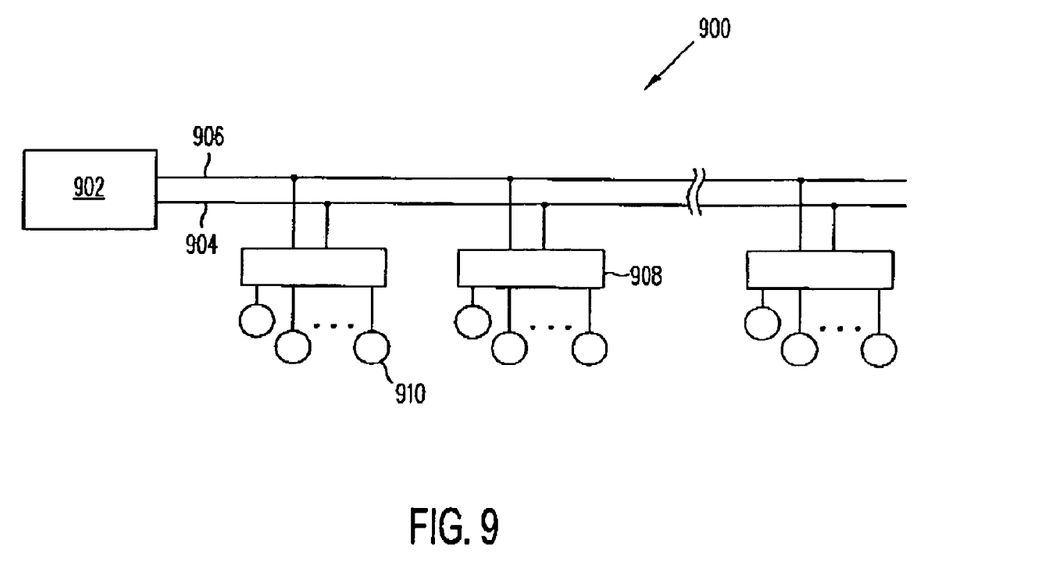
FIG. 9 illustrates a system employing an array of monitoring elements, a single control line, a single signal line, and switches each switching on/off multiple monitoring elements.

While the switches described above have been shown as switching a single monitoring element on/off, it should be recognized that the invention can also employ switches capable of switching multiple monitoring elements. FIG. 9 illustrates an embodiment employing such switches. System 900 includes a controller 902 with a control line 904 and signal line 906. These lines 904-906 are connected to switches 908, which each switch a number of monitoring elements 910 to their on/off states. Control signals sent from the controller 902 along the control line 904 identify certain monitoring elements 910 for switching on/off. The switches 908 then switch these monitoring elements 910 (which can each be actuators, sensors, transducers, or the like) on or off accordingly. If actuation is desired, the controller 902 then transmits signals to those elements 910 that are switched on, so as to cause them to generate stress waves or other diagnostic signals. If sensing is desired, those elements 910 that are switched on can monitor the structure they are attached to, and transmit signals along the signal line 906 for detection by the controller 902.

One of ordinary skill in the art will realize that the invention is not limited to the various embodiments described above. For example, a flexible layer can be employed for convenience, but need not necessarily be used. Various components can also be attached to the flexible layer, or left off, i.e., only the various monitoring elements and lines can be attached to the layer, or their associated controllers or other circuitry can be attached as well. Also, the monitoring elements described above can be piezoelectric transducers, fiber optic sensors, or any other sensors, actuators, or sensor/actuators employed in structural health monitoring. The various lines can also be bundled into single cables for further convenience. For instance, in FIG. 8, all four lines 804-810 can be bundled into a single cable.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description. They are not intended to be exhaustive or to limit the invention to the precise forms disclosed. Many modifications and variations are possible in view of the above teachings. For example, as described above, sensor networks and actuator networks can be utilized separately or in conjunction with each other, and a single network can employ both sensors and actuators. Also, networks can utilize any suitable components as monitoring elements, such as piezoelectric transducers, fiber optic sensors, and the like. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A structural health monitoring system, comprising:
   a plurality of monitoring elements configured for coupling to a structure;
   a plurality of switches each in electrical communication with an associated monitoring element of the plurality of monitoring elements, and each configured to switch the associated monitoring element to an on state and an off state;
   a control line configured for coupling to the structure, and in electrical communication with each switch of the plurality of switches;
   a signal line configured for coupling to the structure, and in electrical communication with each monitoring element of the plurality of monitoring elements; and
   a controller configured to transmit a control signal along the control line so as to switch selected ones of the monitoring elements to the on state or the off state, and configured to perform at least one of transmitting a monitoring signal along the signal line to those monitoring elements switched to the on state so as to initiate a monitoring of the structure, or receiving a sensing signal along the signal line from those monitoring elements switched to the on state so as to facilitate the sensing of the structure.

2. The structural health monitoring system of claim 1 further comprising a flexible substrate configured for attachment to the structure, wherein the plurality of monitoring elements, the plurality of switches, the control line, and the signal line are affixed to the flexible substrate.

3. The structural health monitoring system of claim 2 wherein the controller is affixed to the flexible substrate.

4. The structural health monitoring system of claim 1 wherein each monitoring element of the plurality of monitoring elements is an actuator configured to generate a stress wave in the structure in response to the monitoring signal.

5. The structural health monitoring system of claim 1 wherein each monitoring element of the plurality of monitoring elements is a sensor configured to generate the sensing signal in response to a detected stress wave within the structure.

6. The structural health monitoring system of claim 1 wherein each monitoring element of the plurality of monitoring elements is a piezoelectric transducer configured to generate a stress wave in the structure in response to the monitoring signal, and to generate the sensing signal in response to a detected stress wave within the structure.

7. The structural health monitoring system of claim 1:
   wherein at least one monitoring element of the plurality of monitoring elements is an actuator configured to generate a stress wave in the structure; and
   wherein the structural health monitoring system further comprises a fiber optic sensor configured for coupling to the structure, and configured to sense the generated stress wave in the structure, and to generate a fiber optic sensing signal in response.

8. The structural health monitoring system of claim 7 further comprising a fiber optic sensor data unit configured to receive the fiber optic sensing signal.

9. The structural health monitoring system of claim 1:
   wherein the plurality of monitoring elements further comprises a plurality of sensors and a plurality of actuators;
   wherein the plurality of switches further comprises a plurality of sensor switches each in electrical communication with an associated sensor of the plurality of sensors, and each configured to switch the associated sensor to an on state and an off state, and a plurality of actuator switches each in electrical communication with an associated actuator of the plurality of actuator, and each configured to switch the associated actuator to an on state and an off state;
   wherein the structural health monitoring system further comprises:
      a sensor control line configured for coupling to the structure, and in electrical communication with each switch of the plurality of sensor switches a sensor signal line configured for coupling to the structure, and in electrical communication with each sensor of the plurality of sensors;
      an actuator control line configured for coupling to the structure, and in electrical communication with each switch of the plurality of actuator switches;
      an actuator signal line configured for coupling to the structure, and in electrical communication with each actuator of the plurality of actuators; and
   wherein the controller is further configured to:
      transmit a control signal along the sensor control line so as to switch selected ones of the sensors to the on state or the off state;
      receive a sensing signal along the sensor signal line from those sensors switched to the on state so as to facilitate the sensing of the structure;

transmit a control signal along the actuator control line so as to switch selected ones of the actuators to the on state or the off state; and transmit a monitoring signal along the actuator signal line to those actuators switched to the on state so as to initiate a monitoring of the structure.

10. The structural health monitoring system of claim 9 wherein the actuators and the sensors are each piezoelectric transducers configured to generate a stress wave in the structure in response to the monitoring signal, and to generate the sensing signal in response to a detected stress wave within the structure.

11. The structural health monitoring system of claim 10 wherein each of the piezoelectric transducers is in electrical communication with an associated one of the sensor switches and an associated one of the actuator switches.

12. The structural health monitoring system of claim 1 wherein each switch of the plurality of switches is in electrical communication with multiple ones of the monitoring elements, and is configured to switch each monitoring element of the multiple ones of the monitoring elements to the on state and the off state.

13. In a structural health monitoring system including a plurality of monitoring elements configured for coupling to a structure, the monitoring elements each having an on state and an off state, a method of monitoring the health of a structure, comprising:

selecting ones of the monitoring elements;

switching the selected ones of the monitoring elements to the on state; and at least one of transmitting a monitoring signal to those monitoring elements switched to the on state so as to initiate a monitoring of the structure, or receiving a sensing signal from those monitoring elements switched to the on state so as to facilitate the sensing of the structure;

wherein the transmitting further comprises transmitting the monitoring signal along a single signal line to those monitoring elements switched to the on state.

14. In a structural health monitoring system including a plurality of monitoring elements configured for coupling to a structure, the monitoring elements each having an on state and an off state, a method of monitoring the health of a structure, comprising:

selecting ones of the monitoring elements;

switching the selected ones of the monitoring elements to the on state; and at least one of transmitting a monitoring signal to those monitoring elements switched to the on state so as to initiate a monitoring of the structure, or receiving a sensing signal from those monitoring elements switched to the on state so as to facilitate the sensing of the structure;

wherein the receiving further comprises receiving, along a single sensing line, a sensing signal from those monitoring elements switched to the on state.

15. A computer readable medium having computer executable instructions thereon for a method of monitoring the health of a structure in a structural health monitoring system including a plurality of monitoring elements configured for coupling to the structure, the monitoring elements each having an on state and an off state, the method comprising:

selecting ones of the monitoring elements;

switching the selected ones of the monitoring elements to the on state; and at least one of transmitting a monitoring signal to those monitoring elements switched to the on state so as to initiate a monitoring of the structure, or receiving a sensing signal from those monitoring elements switched to the on state so as to facilitate the sensing of the structure;

wherein the transmitting further comprises transmitting the monitoring signal along a single signal line to those monitoring elements switched to the on state.

16. A computer readable medium having computer executable instructions thereon for a method of monitoring the health of a structure in a structural health monitoring system including a plurality of monitoring elements configured for coupling to the structure, the monitoring elements each having an on state and an off state, the method comprising:

selecting ones of the monitoring elements;

switching the selected ones of the monitoring elements to the on state; and at least one of transmitting a monitoring signal to those monitoring elements switched to the on state so as to initiate a monitoring of the structure, or receiving a sensing signal from those monitoring elements switched to the on state so as to facilitate the sensing of the structure;

wherein the receiving further comprises receiving, along a single sensing line, a sensing signal from those monitoring elements switched to the on state.

* * * * *